US012605043B2

(12) United States Patent
Hase

(10) Patent No.: US 12,605,043 B2
(45) Date of Patent: Apr. 21, 2026

(54) PUSH SWITCH DEVICE OF ENDOSCOPE AND ENDOSCOPE

(71) Applicant: OLYMPUS MEDICAL SYSTEMS CORP., Tokyo (JP)

(72) Inventor: Hidenosuke Hase, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 141 days.

(21) Appl. No.: 18/768,454

(22) Filed: Jul. 10, 2024

(65) Prior Publication Data

US 2024/0358225 A1 Oct. 31, 2024

Related U.S. Application Data

(63) Continuation of application No. PCT/JP2022/001404, filed on Jan. 17, 2022.

(51) Int. Cl.
*A61B 1/00* (2006.01)
(52) U.S. Cl.
CPC ...... *A61B 1/00066* (2013.01); *A61B 1/00103* (2013.01)
(58) Field of Classification Search
None
See application file for complete search history.

(56) References Cited

U.S. PATENT DOCUMENTS 4,845,555 A 7/1989 Yabe et al.
11,089,942 B2 * 8/2021 Kishioka .............. A61B 1/0052

2007/0038023 A1 * 2/2007 Uchimura .......... A61B 1/00016
600/156
2011/0095067 A1 * 4/2011 Ohdaira ........... A61B 17/07207
606/49
2012/0165605 A1 * 6/2012 Yamazaki .......... A61B 1/00066
600/106
2014/0357952 A1 * 12/2014 Krohn ................ A61B 1/00006
600/112
2021/0212554 A1 * 7/2021 Uchida .............. A61B 1/00066
2021/0228062 A1 * 7/2021 Edwards ........... G02B 23/2461
(Continued)

FOREIGN PATENT DOCUMENTS

JP S63197430 A 8/1988
JP H02135002 U 11/1990
(Continued)

OTHER PUBLICATIONS

International Search Report dated Apr. 5, 2022 issued in PCT/JP2022/001404.

*Primary Examiner* — Mohammad J Rahman
(74) *Attorney, Agent, or Firm* — Scully, Scott, Murphy & Presser, P.C.

(57) ABSTRACT

A push switch device of an endoscope includes an electric operation switch and a switch button that pushes the operation switch. The switch button includes: a shaft inserted through a hole of a case body of an operation portion; a button top arranged outside the case body and configured to receive an operational force orthogonal to the shaft; a spherical-shaped pusher configured to push in the operation switch by receiving the operational force; and a flange having an arc and provided at midway of the shaft, the flange being configured such that a part thereof abuts against an inside of the operation portion when the shaft is tilted by the operational force.

20 Claims, 11 Drawing Sheets

(56)        References Cited

U.S. PATENT DOCUMENTS

| 2022/0236759 | A1 | 7/2022 | Gorai et al. |
| 2022/0240755 | A1 | 8/2022 | Kimura et al. |
| 2022/0244751 | A1 | 8/2022 | Kimura et al. |
| 2022/0246374 | A1 | 8/2022 | Gorai et al. |
| 2023/0127909 | A1* | 4/2023 | Ichimura ............ A61B 1/00057 |
| | | | 600/156 |

FOREIGN PATENT DOCUMENTS

| JP | H08191789 | A | 7/1996 |
| JP | 2010272322 | A | 12/2010 |
| JP | 4763093 | B2 | 8/2011 |
| JP | 5519878 | B2 | 6/2014 |
| JP | 2019071254 | A | 5/2019 |
| WO | 2013154106 | A1 | 10/2013 |
| WO | 2021085289 | A1 | 5/2021 |

* cited by examiner

PUSH SWITCH DEVICE OF ENDOSCOPE AND ENDOSCOPE

CROSS-REFERENCE TO RELATED APPLICATION

This application is a continuation application of PCT/JP2022/001404 filed on Jan. 17, 2022, the entire contents of which are incorporated herein by this reference.

BACKGROUND OF THE INVENTION

1. Field of the Invention

The present disclosure relates to a push switch device of an endoscope, and an endoscope, the push switch device being configured to operate a switch that makes an electric circuit conductive.

2. Description of the Related Art

In recent years, endoscopes have been widely used in medical fields and industrial fields. Endoscopes are capable of performing observation, treatment, and the like of a site to be examined in a subject or an object by inserting an elongated insertion portion into the subject or object. Such endoscopes include, at an operation portion thereof, button switches for operating various kinds of functions such as activation, stop, selection, etc.

For example, Japanese Patent Application Laid-Open Publication No. 2010-272322 discloses a push button switch including a hollow guide cylinder fitted and fixed water-tightly in a through hole provided in a casing of an operation portion of an endoscope, a movable pushing member that is displaced in the guide cylinder, and a switch portion provided at a lower portion in the guide cylinder and being configured to abut against the movable pushing member.

In addition, the international publication No. WO2013/154106 discloses a push switch device incorporating a switch portion configured to perform switching operation by a stress having a component in a vertical direction with respect to an outer surface of an operation portion of a hand-held instrument that is operated by an operator.

SUMMARY OF THE INVENTION

A push switch device of an endoscope according to one aspect of the present disclosure is provided at an operation portion configured to be grasped by an operator, and the push switch device includes: an operation switch configured to make an electric circuit conductive; and a switch button configured to push the operation switch. The switch button includes: a shaft arranged by being inserted through a hole formed in a case body of the operation portion; a button top connected to one end of the shaft and arranged outside the case body, the button top being configured to receive an operational force in a direction orthogonal to the shaft; a pusher having a shape including at least a part of a spherical body having an outer diameter larger than an outer diameter of the shaft, the pusher being configured to move when the button top receives the operational force, to push in the operation switch arranged facing the pusher; and a flange provided at midway of the shaft and including an arc which is on an outer surface of the flange and has a diameter larger than an outer diameter of the button top, the flange being housed in an inside of the operation portion and configured such that a part of the outer surface is brought into a state abuttable against the inside of the operation portion when the shaft is tilted by the operational force applied to the button top.

An endoscope according to one aspect of the present disclosure includes: an operation portion configured to be grasped by an operator; and a push switch device provided at the operation portion. The push switch device includes: an operation switch configured to make an electric circuit conductive; and a switch button configured to push the operation switch. The switch button includes: a shaft arranged by being inserted through a hole formed in a case body of the operation portion; a button top connected to one end of the shaft and arranged outside the case body, the button top being configured to receive an operational force in a direction orthogonal to the shaft; a pusher having a shape including at least a part of a spherical body having an outer diameter larger than an outer diameter of the shaft, the pusher being configured to move when the button top receives the operational force, to push in the operation switch arranged facing the pusher; and a flange provided at midway of the shaft and including an arc which is on an outer surface of the flange and has a diameter larger than an outer diameter of the button top, the flange being housed in an inside of the operation portion and configured such that a part of the outer surface is brought into a state abuttable against the inside of the operation portion when the shaft is tilted by the operational force applied to the button top.

DETAILED DESCRIPTION OF THE PREFERRED EMBODIMENT(S)

Hereinafter, description will be made by taking an endoscope as an insertion instrument, which relates to a present disclosure, as an example. Note that each of the drawings based on each embodiment is a pattern diagram, and care should be taken to the fact that the relationship between the thicknesses and widths of the respective parts, a ratio of the thickness of a certain part to that of another part, and the like are different from the actual ones, and there is a case where the respective drawings include parts in which the relationships and ratios among the dimensions are different.

Figure 1:
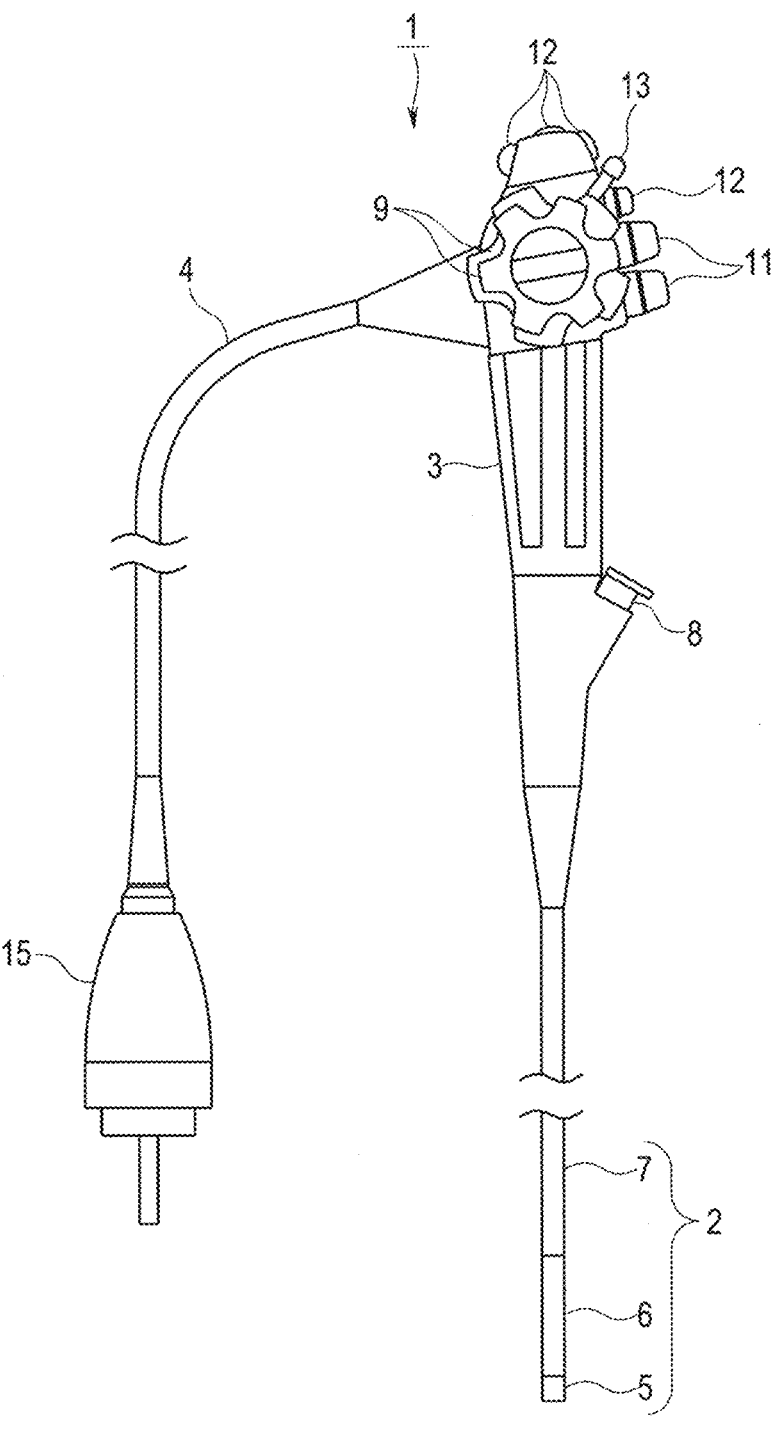
FIG. 1 is a side view showing a configuration of an endoscope in the present disclosure.
Figure 2:
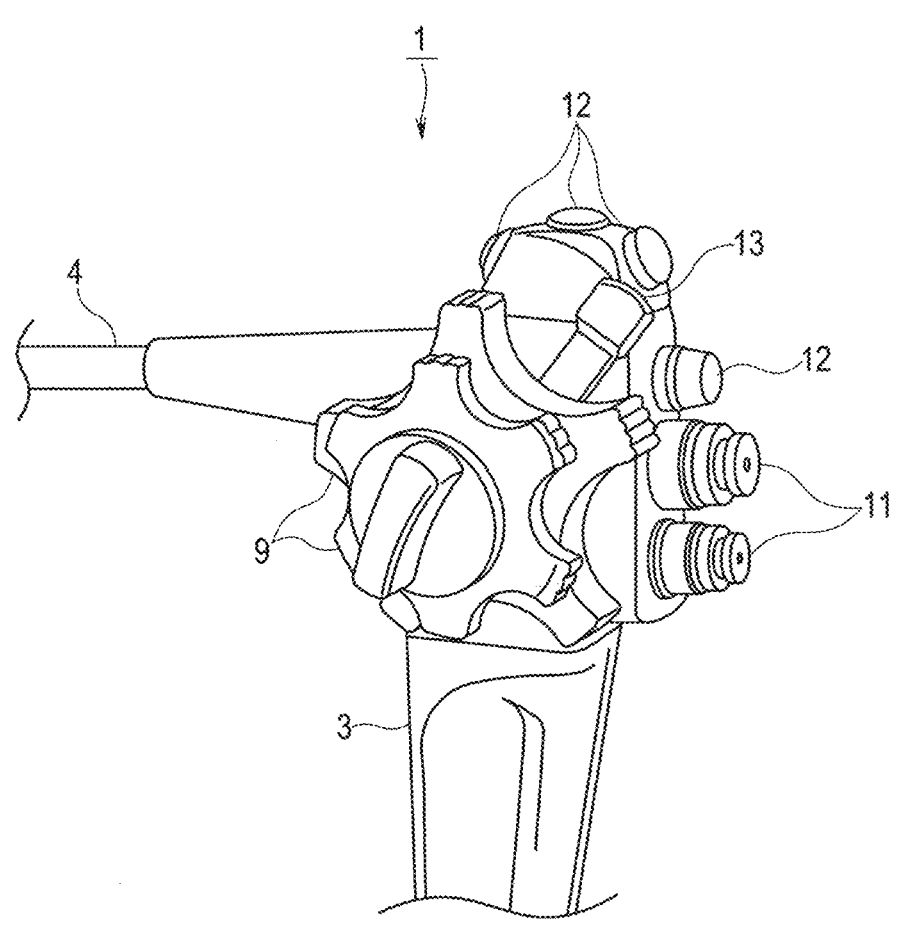
FIG. 2 is a perspective view partially showing a configuration of an upper portion of an operation portion of the endoscope in the present disclosure.

First, description will be made on a schematic configuration of an endoscope 1 of a present embodiment. As shown in FIG. 1 and FIG. 2, the endoscope 1 of the present embodiment mainly includes an insertion portion 2, which is a long member, configured to be insertable into a subject or an object, an operation portion 3 located at the proximal end of the insertion portion 2, and a universal cord 4, which is a composite cable, extended from the side portion of the operation portion 3.

The insertion portion 2 includes a distal end portion 5, a bendable bending portion 6, and a flexible tube portion 7 having flexibility, which are connected continuously. The distal end portion 5 is disposed at the distal end of the insertion portion. The bending portion 6 is disposed on the proximal end side of the distal end portion 5. The flexible tube portion 7 is disposed on the proximal end side of the bending portion 6 and connected to the distal end side of the operation portion 3.

The operation portion 3 includes a forceps plug 8, which is a forceps port cap, at a treatment instrument insertion port communicated with a treatment instrument insertion channel (not shown) as an endoscope conduit. In addition, the operation portion 3 includes: an angle knob 9 for operating bending of the bending portion 6; buttons 11 such as a gas/liquid feeding button for controlling feeding operation of a fluid from a fluid feeding section (not shown) provided at the distal end portion 5; a plurality of switch buttons 12 configured to operate freeze of an endoscopic image, release of image pickup, and the like; and a fixing lever 13 for fixing the angle knob 9.

The universal cord 4 includes, on the proximal end side thereof, an endoscope connector 15 configured to be connected to a video processor (not shown) including a light source apparatus. Illumination light emitted from a light source of the video processor is transmitted to a light guide bundle, not shown, which is inserted through the universal cord 4, the operation portion 3, and the insertion portion 2, and then the illumination light is emitted from an illumination window (not shown) provided at the distal end portion 5. Note that the endoscope 1 may be configured such that a light source such as an LED is provided as an illumination device at the distal end portion 5.

In addition, the distal end portion 5 includes an observation window (not shown), and incorporates an image sensor (not shown) that photoelectrically converts photographing light entered from the observation window. An image pickup cable extended from the image sensor is also inserted through the insertion portion 2, the operation portion 3, and the universal cord 4, to reach the endoscope connector 15.

Note that the endoscope 1 may preferably be a single-use endoscope which is disposable (used once) and discarded after use. However, it is needless to say that the endoscope 1 may be a reuse product to be reused after being subjected to disinfection and sterilization processing.

Hereinafter, description will be made in detail below on a push switch device 10 of the endoscope 1 according to the present embodiment. Note that the push switch device 10 will be described as the one having a configuration including a plurality of switch buttons 12 provided on the operation portion 3 of the above-described endoscope 1.

Figure 3:
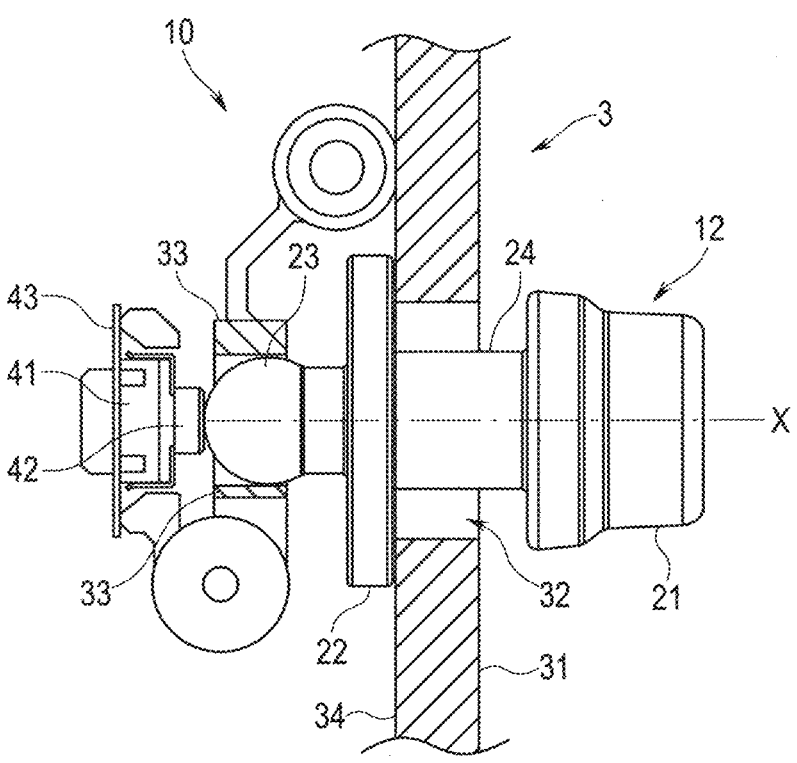
FIG. 3 is a partial cross-sectional view showing a configuration of a push switch device of the endoscope in the present disclosure.

As shown in FIG. 3, the push switch device 10 includes the switch buttons 12 disposed on a case body 31 as an exterior member of the operation portion 3, and a switch 41 disposed in the operation portion 3 and configured to make an electric circuit conductive.

Figure 4:
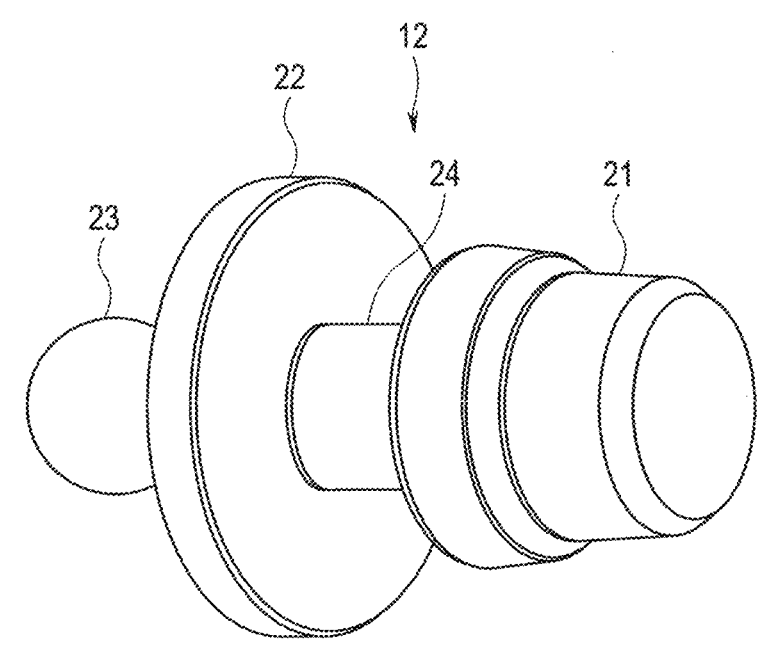
FIG. 4 is a perspective view showing a configuration of a switch button in the present disclosure.
Figure 5:
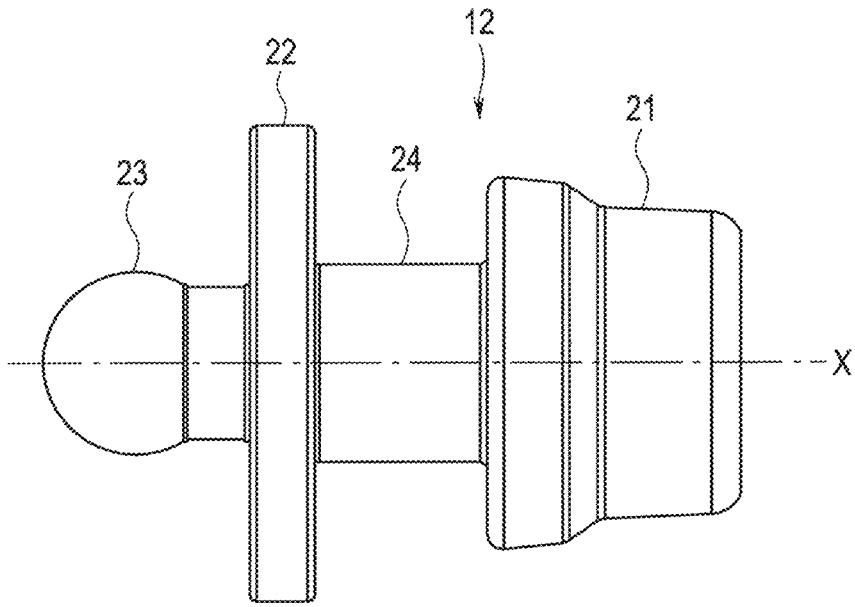
FIG. 5 is a side view showing the configuration of the switch button in the present disclosure.

The switch button 12 includes, as shown in FIG. 4 and FIG. 5, a button top 21, a flange 22, and a pusher 23. The button top 21 has a substantially truncated cone shape (shape including a truncated cone) and is connected to one end of a shaft 24 which is along a longitudinal axis X. The flange 22 is provided at midway of the shaft 24, and has an arc and formed in a disk (circular) shape around the shaft 24. The pusher 23 has a shape including a substantially spherical body (at least a part of the spherical body) including at least a part of a spherical surface connected to the other end of the shaft 24. The flange 22 is housed in an inside of the operation portion 3. The arc on the outer surface of the flange 22 has an outer diameter larger than an outer diameter of the button top 21. An outer diameter of at least a part of the spherical body of the pusher 23 is larger than an outer diameter of a part of the shaft 24 located between the flange 22 and the pusher 23.

Referring back to FIG. 3, the switch button 12 is configured such that a part of the shaft 24 located between the button top 21 and the flange 22 is arranged in a hole 32 formed in the case body 31 of the operation portion 3. In such a configuration, the switch button 12 is provided such that the button top 21 is positioned outside the case body 31 that forms the outer surface of the operation portion 3, and the flange 22 is provided inside the operation portion 3, with a predetermined clearance (gap) in the direction along the shaft 24 with respect to the inner surface of the case body 31.

Note that the flange 22 has an outer diameter larger than the size of the outer shape of the pusher 23.

The hole 32 of the case body 31 has a hole diameter smaller than the outer diameter of the flange 22 and larger than the outer diameter of the shaft 24. Therefore, the hole 32 has a predetermined clearance (gap) with respect to the shaft 24. In other words, around the hole 32, an inner surface 34 of the case body 31, which receives the surface of the flange 22 in all radial directions around the shaft 24, is arranged.

Although not shown, the case body 31 is configured, for enabling the switch button 12 to be mounted in the hole 32, such that a plurality of case members that divide the case body 31 at a part where the switch button 12 passes through the hole 32 (for example, two case members which divide the case body 31 into two at substantially the center of the hole 32) are assembled at a seam portion.

The pusher 23 is rotatably supported by a plurality of, i.e., four supporting members 33 in this embodiment, with the switch button 12 being mounted to the case body 31 of the operation portion 3, the supporting members being a housing body provided in the operation portion 3.

Figure 6:
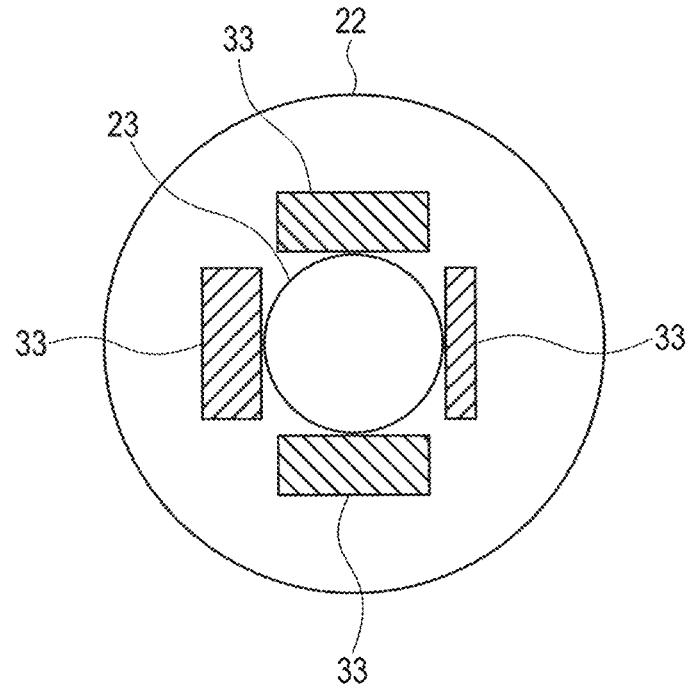
FIG. 6 is a partial cross-sectional view describing a state where a pusher of the switch button is supported, in the present disclosure.

Specifically, as shown in FIG. 6, the pusher 23 of the switch button 12 is arranged inside the operation portion 3, such that four directions (here, up, down, left, and right directions) around the shaft 24 are covered with the four block-shaped supporting members 33.

Thus, the switch button 12 is configured such that the periphery of the pusher 23 is supported by the four supporting members 33, to thereby allow the up, down, left, and right directions around the shaft 24 of the pusher 23 to be supported, and allow the switch button 12 to move in a thrust direction of the pusher 23, i.e., in the direction in which the shaft 24 advances and retracts.

Note that the supporting members 33 are protruded portions provided in the case body 31 and protruded inward. The number of the supporting members that support the pusher 23 is not limited to four, but may be any number of three or more.

The switch 41 is mounted on a substrate 43 and fixed in the operation portion 3. The switch 41 includes a protrusion button 42 which is an operation button configured to protrude and retract. The protrusion button 42 is provided at a position facing and abutting against the pusher 23 of the switch button 12. The pusher 23 thus abuts against the protrusion button 42, to thereby enable the backlash of the switch button 12 to be suppressed.

Note that the switch 41 is a tact switch in the present configuration, and may be of any configuration in which the protrusion button 42 as a plunger is a momentary action button or an alternate action button.

Figure 7:
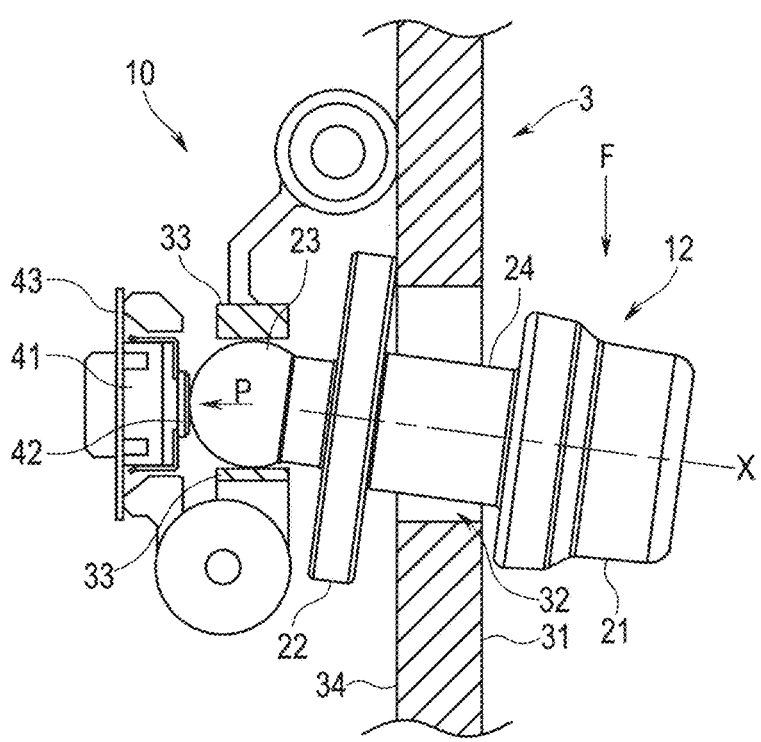
FIG. 7 is a partial cross-sectional view showing the configuration of the push switch device of the endoscope in a state where the switch button is pushed downward, in the present disclosure.
Figure 8:
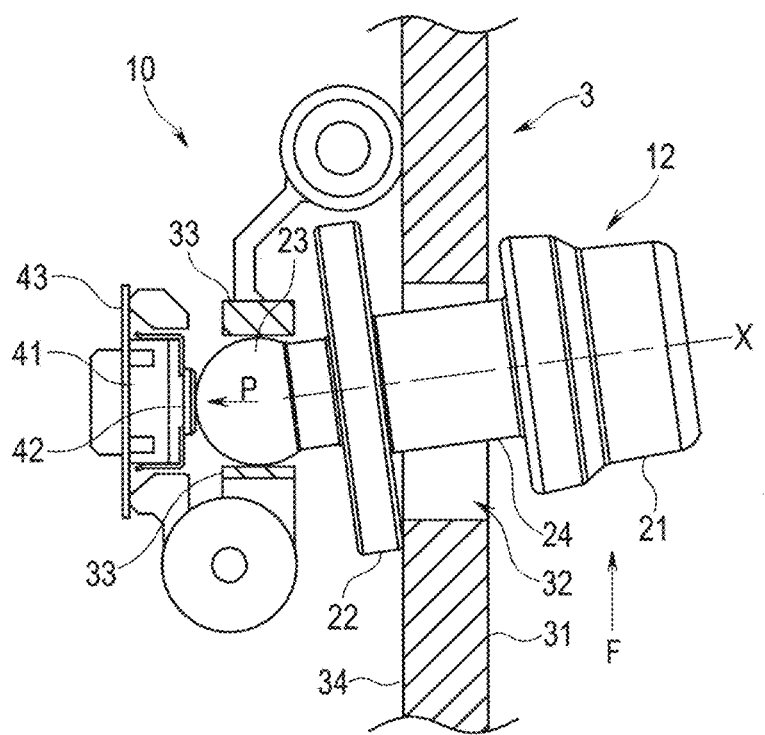
FIG. 8 is a partial cross-sectional view showing the configuration of the push switch device of the endoscope in a state where the switch button is pushed upward, in the present disclosure.

As shown in FIG. 7 and FIG. 8, in the push switch device 10 thus configured, the switch button 12 receives an operational force applied from outside by a finger of a user, or the like, to the circumferential surface of the button top 21 (shown as the downward arrow mark F in FIG. 7, and as upward arrow mark F in FIG. 8), to be pushed, and thereby the longitudinal axis X of the switch button 12 is tilted.

At this time, in the switch button 12, a part of the flange 22 abuts against only the inner surface 34 which serves as an abutting surface of the case body 31, to be a fulcrum, and the pusher 23 thrusts to move in the inner direction (arrow mark P) of the operation portion 3.

In other words, when the switch button 12 is pushed from the circumferential surface of the button top 21, which is a direction orthogonal to the shaft 24, the switch button 12 is tilted due to the presence of the clearance (gap) between the hole 32 of the case body 31 and the shaft 24. At this time, in the switch button 12, the pusher 23 is rotatably supported by the supporting members 33, to thereby guide the movement of the flange 22.

Then, a part of the flange 22 (a part of the outer surface (arc) of the flange 22), which is on the side in the direction opposite to the tilted direction, abuts (contacts) against only the inner surface 34 (contact surface) of the case body 31, to be a fulcrum, and the switch button 12 moves so as to sink into the operation portion 3.

In other words, the flange 22 tilts along the shaft 24 due to the clearance (gap) with respect to the inner surface 34 of the case body 31 of the operation portion 3, and a part of the outer circumferential surface of the flange 22 contacts the inner surface 34, and thereby the switch button 12 moves so as to sink into the operation portion 3.

Note that the abutting of a part of the flange 22 against the inner surface 34 of the case body 31 is not limited to direct abutting of the flange 22 against the inner surface of the case body 31.

The abutting of a part of the flange 22 includes abutting of the arc of the flange against the inside of the case body 31, that is, the inner surface of the case body 31 in a structure of the operation portion 3.

For example, a part of the flange 22 may abut against the inner surface of the case body 31 through a thin plate provided so as to contact the inner surface of the case body 31, or a part of the flange 22 may abut against a thin structure in the operation portion 3, which is provided adjacent to the inner surface of the case body 31.

At this time, the pusher 23 is in the state where the periphery thereof is supported by the four supporting members 33, which causes the pusher 23 to move toward the switch 41 while rotating. With such a movement of the pusher 23, the pusher 23 pushes in the protrusion button 42, and thereby the switch 41 is turned on.

In addition, in the push switch device 10, by releasing the tilt of the switch button 12 (by returning to the initial state), the push-in of the protrusion button 42 by the pusher 23 is also released and the switch 41 is turned off. Note that the push switch device 10 may be configured such that the switch 41 is turned off by performing operation of pushing in (operation of titling) the switch button 12 again.

Note that the larger the outer diameter of the flange 22 is, the less tilting of the switch button 12 is required to push the protrusion button 42 of the switch 41. In other words, the stroke of sinking of the switch button 12 into the operation portion 3 can be increased.

Figure 9:
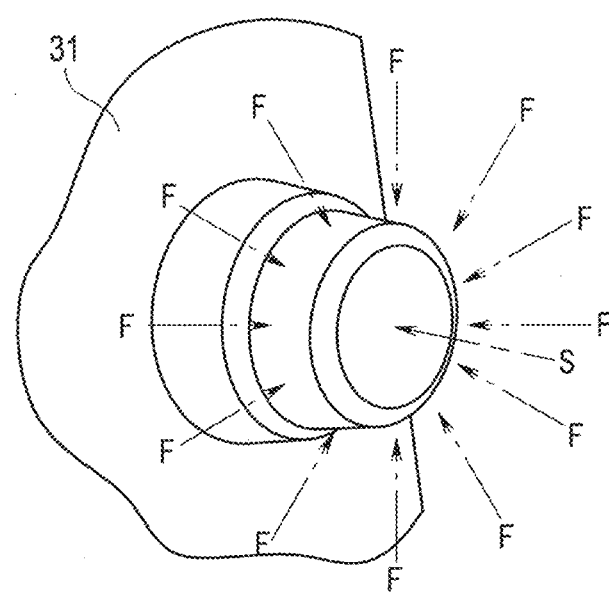
FIG. 9 is a perspective view describing an operation direction of the switch button in the present disclosure.
Figure 10:
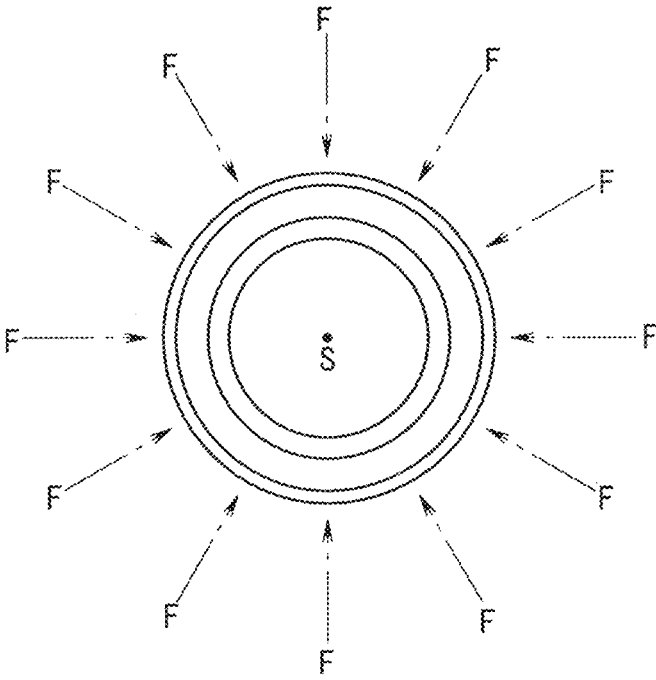
FIG. 10 is a plan view describing the operation direction of the switch button in the present disclosure.

As described above, the push switch device 10 is configured such that the switch 41 can be turned on (off) even if the circumferential surface of the button top 21 of the switch button 12 is pushed in any direction (F direction shown in the drawings) in 360 degrees around the circumferential surface (longitudinal axis X), as shown in FIG. 9 and FIG. 10. In other words, the switch 41 can be turned on (off) even if the switch button 12 is pushed from the circumference of the button top 21 orthogonal to the shaft 24.

Note that, needless to say, the push switch device 10 is configured such that the switch 41 can be turned on (off), even if the button top 21 of the switch button 12 is pushed in the direction (P direction) along the longitudinal axis X.

Thus, the push switch device 10 includes: the switch button 12 including the round-shaped flange 22 and the spherical-shaped pusher 23; the inner surface 34 of the case body 31, which is a surface that receives the flange 22; and the plurality of supporting members 33 that support the up, down, left, and right of the switch button 12 so as to be movable in the thrust direction. The push switch device 10 has a structure in which the on/off operation of the switch 41 can be performed even if the button switch 12 is pushed in every direction of 360 degrees around the button top 21, by providing the hole 32 of the case body 31, the hole 32 having the clearance that allows the switch button 12 to be tilted up to a predetermined range.

Therefore, the push switch device 10 of the endoscope 1 is capable of improving the operability of the switch button 12 that is operated by a user while grasping the operation portion 3.

Note that the push switch device 10 of the endoscope 1 has a simple structure in which the switch button 12 for turning on and off the switch 41 is provided with the flange 22 and pusher 23, the plurality of supporting members 33 that support the pusher 23 are provided in the case body 31 of the operation portion 3, and the flange 22 is received by the inner surface 34 of the case body 31. With such a simple structure, the number of components can be reduced, and assembly workability is improved, compared with a conventional device. As a result, the push switch device 10 can contribute to the cost reduction of the endoscope 1.

The present disclosure is achieved in view of the above-described demands, and an object of the present disclosure is to provide the push switch device of the endoscope, and the endoscope that have excellent operability and are inexpensive with a simple configuration.

First Modified Example

Next, various configurations for suppressing the backlash of the switch button 12 will be described below as a modified example.

Figure 11:
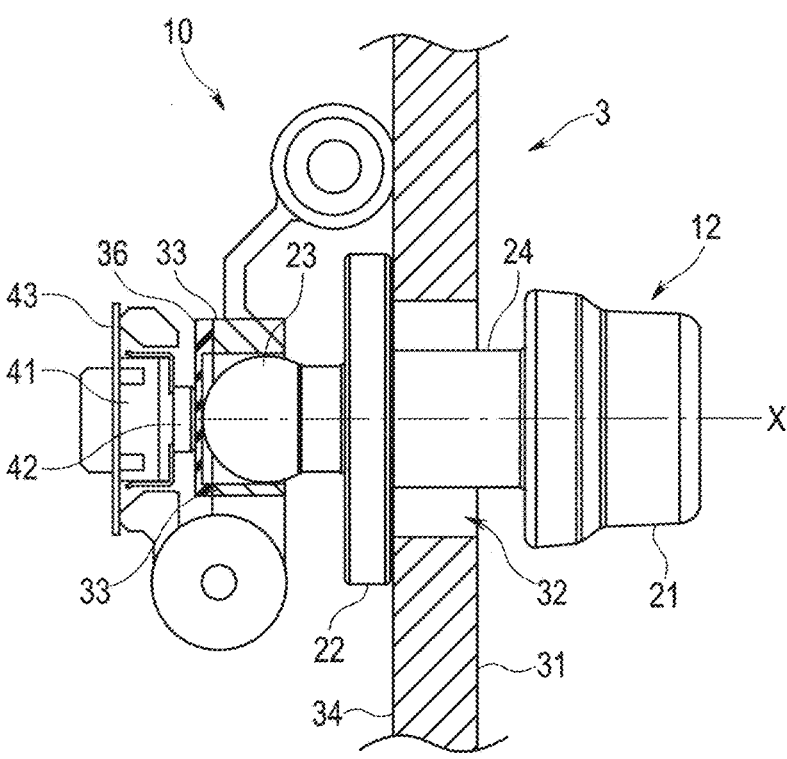
FIG. 11 is a partial cross-sectional view showing a configuration of a push switch device of an endoscope, in which a rubber sheet is provided between a switch and a pusher, in a first modified example.

As shown in FIG. 11, a rubber sheet 36, which is an elastic member, is provided between the pusher 23 of the switch button 12 and the protrusion button 42 of the switch 41, to thereby be capable of suppressing the backlash of the switch button 12. The rubber sheet 36 is provided so as to contact at least one of the pusher 23 and the protrusion button 42. Note that the rubber sheet 36 is fixed by an adhesive or the like to the plurality of supporting members 33.

Figure 12:
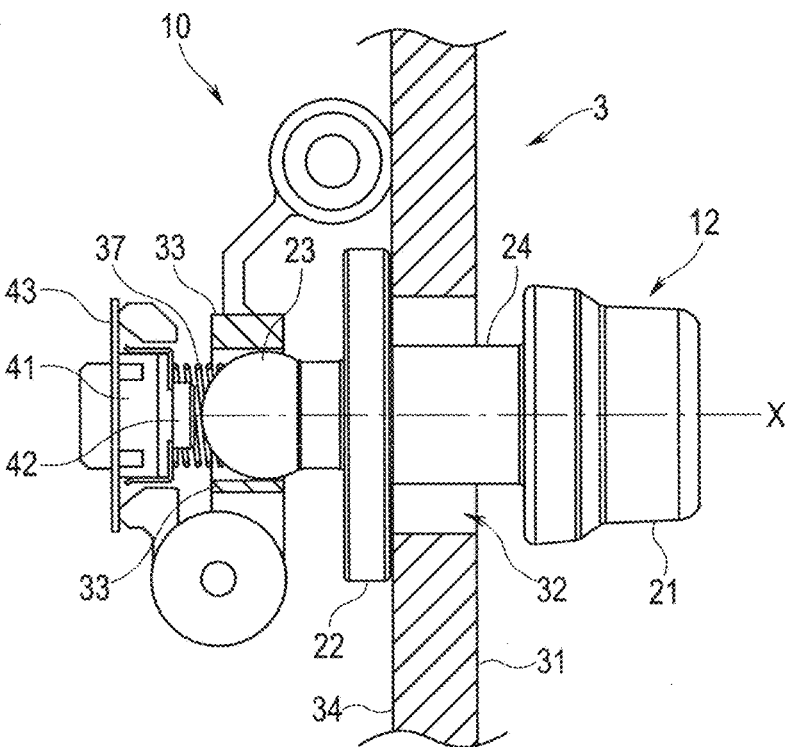
FIG. 12 is a partial cross-sectional view showing a configuration of the push switch device of the endoscope, in which a spring is provided between the switch and the pusher, in the first modified example.

As shown in FIG. 12, by providing a spring 37, which is a biasing member configured to bias the pusher 23 of the switch button 12 along the longitudinal axis X, to thereby bias the switch button 12 located outside the operation portion 3 toward the side of the button top 21, the backlash of the switch button 12 can be suppressed. Note that the spring 37 is provided such that one end thereof abuts against the switch 41 in this configuration.

Figure 13:
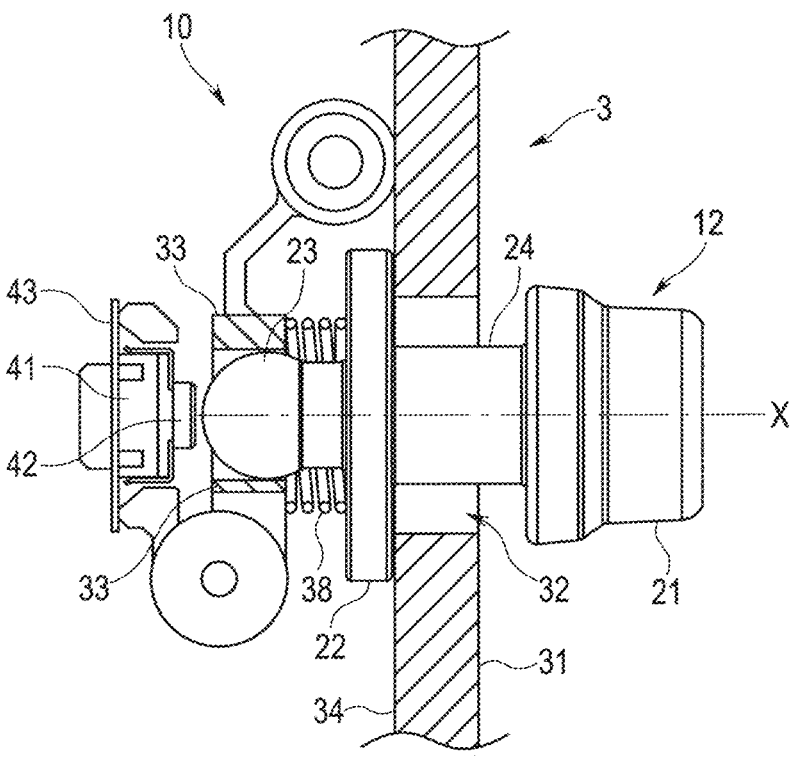
FIG. 13 is a partial cross-sectional view showing a configuration of the push switch device of the endoscope, in which a spring configured to bias a flange is provided, in the first modified example.

As shown in FIG. 13, by providing a spring 38, which is a biasing member configured to bias the flange 22 of the switch button 12 along the longitudinal axis X, to thereby bias the switch button 12 located outside the operation portion 3 toward the side of the button top 21, the backlash of the switch button 12 can be suppressed. Note that the spring 38 is provided such that one end thereof abuts against the plurality of supporting members 33 in this configuration.

Figure 14:
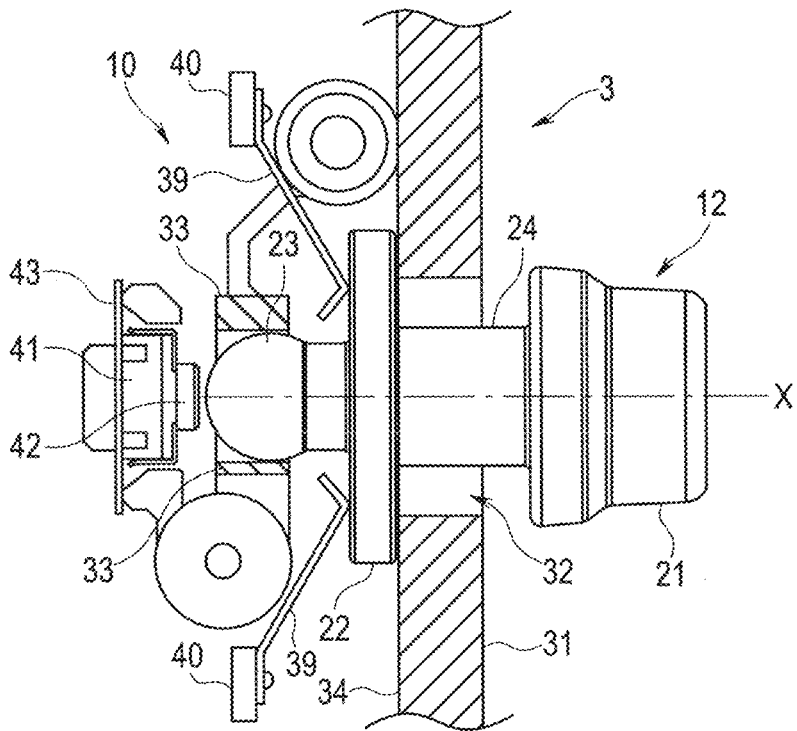
FIG. 14 is a partial cross-sectional view showing a configuration of the push switch device of the endoscope, in which a plate spring configured to bias the flange is provided, in the first modified example.

As shown in FIG. 14, by providing a plurality of plate springs 39, which are biasing members configured to bias the flange 22 of the switch button 12 along the longitudinal axis X, to thereby bias the switch button 12 located outside the operation portion 3 toward the side of the button top 21, the backlash of the switch button 12 can be suppressed. Note that the plurality of plate springs 39 are provided such that end portions thereof are fixed with screws to a pedestal 40 formed in the case body 31 in this configuration.

Second Modified Example

Next, various configurations in which the configuration of the flange 22 of the switch button 12 is changed will be described below as a modified example.

Figure 15:
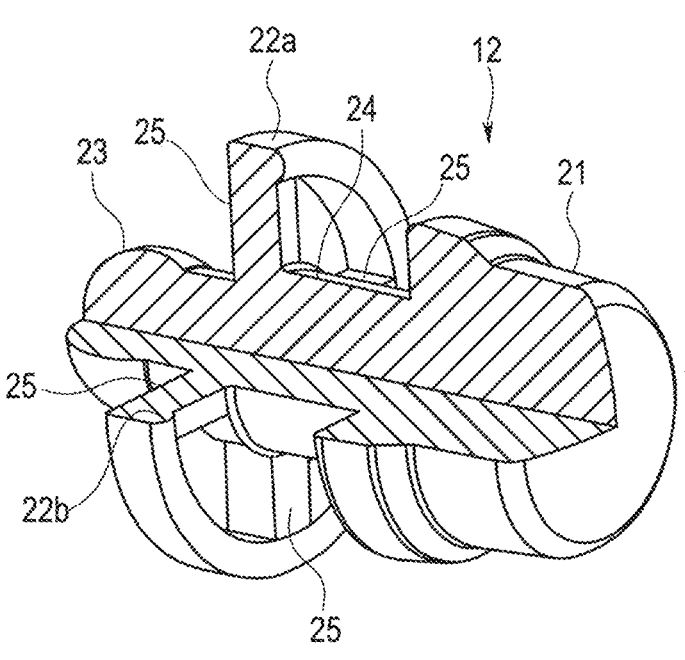
FIG. 15 is a perspective cross-sectional view showing a configuration of a switch button including a ring and a plurality of spokes in a second modified example.
Figure 16:
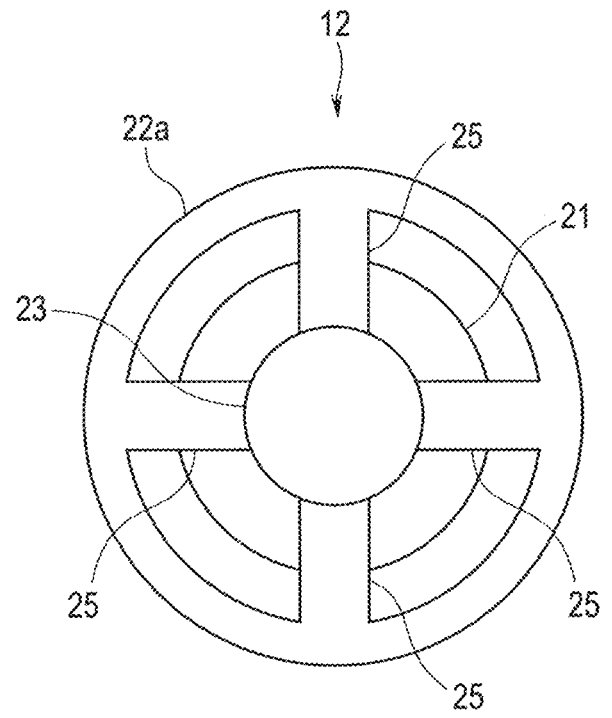
FIG. 16 is a plan view showing the configuration of the switch button including the ring and the plurality of spokes in the second modified example.

As shown in FIG. 15 and FIG. 16, the switch button 12 includes, instead of the disk-shaped flange 22, a flange including a ring 22a and a plurality of, i.e., four spokes 25 provided radially and connecting the ring 22a and the shaft 24.

Figure 17:
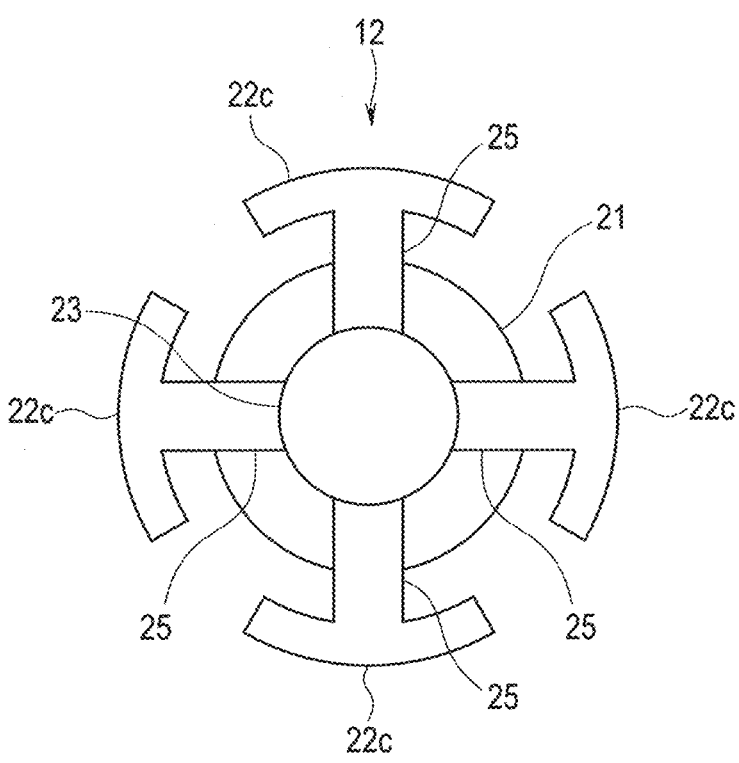
FIG. 17 is a plan view showing a configuration of the switch button including a plurality of arc-shaped members and the plurality of spokes in the second modified example.

The ring 22a includes, on the entire circumference thereof, a protruded portion 22b having an arc-shaped cross section and configured to abut against the inner surface 34 of the case body 31. In addition, as shown in FIG. 17, the ring 22a of the switch button 12 may be provided in plural numbers, that is, the flange may be configured to include four arc members 22c in this modified example. With such a shape of the flange, weight reduction of the switch button 12 can be achieved.

Third Modified Example

Next, various configurations of the pusher 23 of the switch button 12 will be described below as a modified example.

Figure 18:
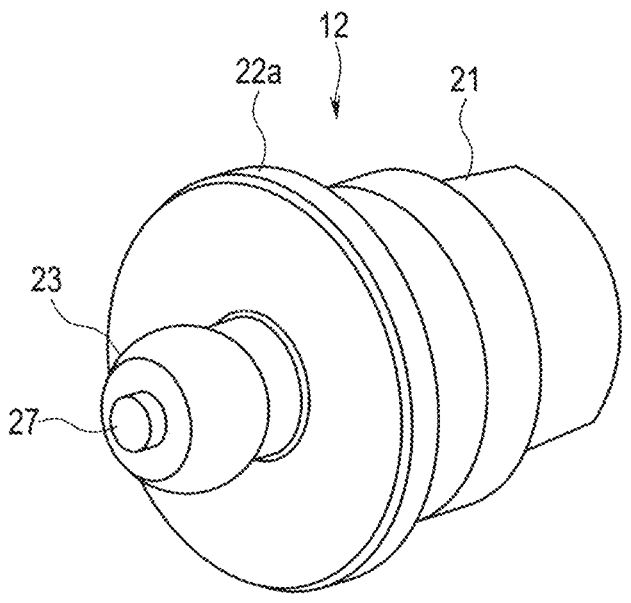
FIG. 18 is a perspective view showing a configuration of a pusher including a columnar protruded portion in a third modified example.
Figure 19:
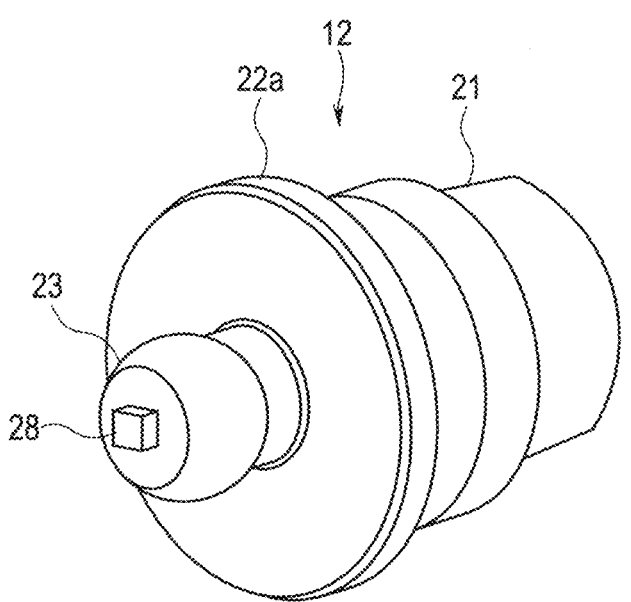
FIG. 19 is a perspective view showing a configuration of the pusher including a square columnar protruded portion in the third modified example.

A part of the pusher 23, the part being configured to push the protrusion button 42 of the switch 41, may be formed as a columnar protruded portion 27 as shown in FIG. 18, or may be formed as a square columnar protruded portion 28 as shown in FIG. 19.

Fourth Modified Example

Figure 20:
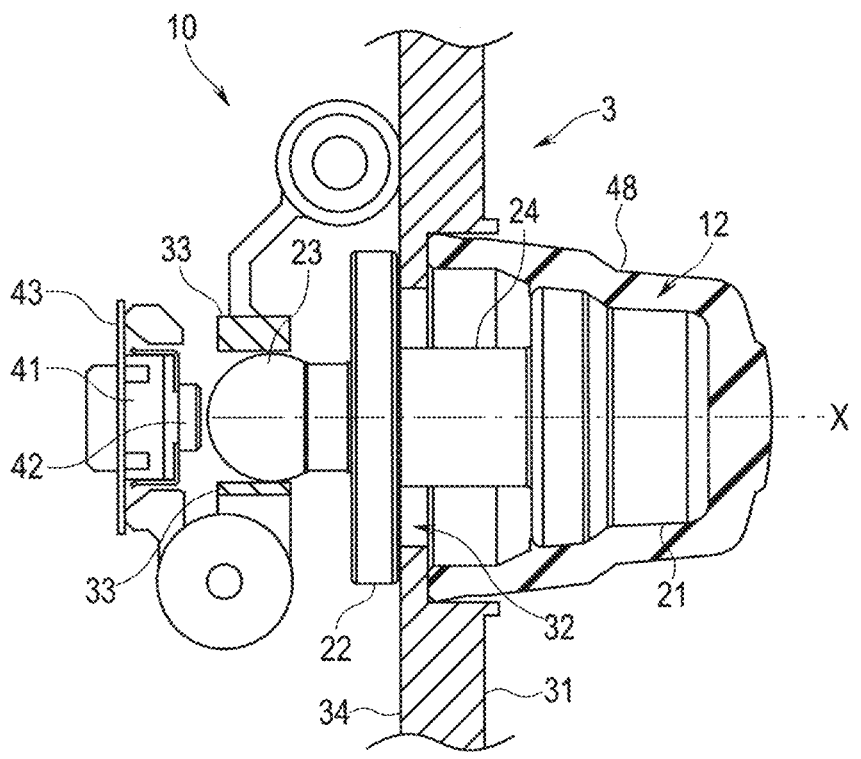
FIG. 20 is a partial cross-sectional view showing a configuration of a push switch device of an endoscope, in which a rubber cover is provided on a switch button, in a fourth modified example.

As shown in FIG. 20, the switch button 12 may be provided with a rubber cover 48 that covers the outer surface of the button top 21. The rubber cover 48 is fixed to the case body 31 of the operation portion 3 in a watertight manner (maintain the watertightness in the operation portion 3), which provides a configuration of the push switch device 10 preferable for not only a single-use endoscope 1 but also a reuse endoscope 1.

Furthermore, by providing the rubber cover 48, the backlash of the switch button 12 can be suppressed. Note that the rubber cover 48 and the button top 21 may preferably be fixed to each other by an adhesive, or by means such as engagement at a fixing part, in order to prevent mutual displacement, but may not necessarily be fixed to each other, for the purpose of facilitating the manufacturing steps.

The disclosure recited in the above-described embodiment and the modified examples is not limited to the embodiment and the modified examples, and various modifications are possible at the practical stage in a range without departing from the gist of the disclosure. Furthermore, each of the above embodiment and modified examples includes the disclosures at various stages, and various disclosures can be extracted by appropriately combining a plurality of disclosed components.

For example, even if some of the components are removed from all the components shown in the above embodiment and modified examples, a configuration from which the components are eliminated can be extracted as a disclosure insofar as the recited problem can be solved and the recited effects of the disclosure can be obtained.

9

10

What is claimed is:

1. A push switch device of an endoscope, which is provided at an operation portion configured to be grasped by an operator, the push switch device comprising:

an operation switch configured to make an electric circuit conductive; and a switch button configured to push the operation switch, wherein the switch button comprises:

a shaft arranged by being inserted through a hole formed in a case body of the operation portion;

a button top connected to one end of the shaft and arranged outside the case body, the button top being configured to receive an operational force in a direction orthogonal to the shaft;

a pusher having a shape including at least a part of a spherical body having an outer diameter larger than an outer diameter of the shaft, the pusher being configured to move when the button top receives the operational force, to push in the operation switch arranged facing the pusher; and a flange provided at midway of the shaft and including an arc which is on an outer surface of the flange and has a diameter larger than an outer diameter of the button top, the flange being housed in an inside of the operation portion and configured such that a part of the outer surface is brought into a state abuttable against the inside of the operation portion when the shaft is tilted by the operational force applied to the button top.

2. The push switch device of the endoscope according to claim 1, wherein the pusher is arranged facing the operation switch such that an outer circumference of the pusher around the shaft is rotatably supported by a housing body provided in the operation portion and configured to hold the switch button.

3. The push switch device of the endoscope according to claim 1, wherein the pusher rotates to move in a thrusting motion, when the button top receives the operational force.

4. The push switch device of the endoscope according to claim 1, wherein the shaft further extends between the pusher and the flange, and the button top has a shape including a truncated cone.

5. The push switch device of the endoscope according to claim 4, wherein the pusher is rotatably supported by a housing body, and thereby the flange is guided.

6. The push switch device of the endoscope according to claim 5, wherein the pusher is configured such that at least a part of the spherical body is rotatably supported by a plurality of supporting members of the housing body.

7. The push switch device of the endoscope according to claim 1, wherein the pusher is provided in a state directly in contact with the operation switch.

8. The push switch device of the endoscope according to claim 1, further comprising an elastic member provided in a clearance between the pusher and the operation switch, the elastic member being in contact with at least one of the pusher and the operation switch.

9. The push switch device of the endoscope according to claim 1, further comprising a biasing member provided between the pusher and the operation switch, the biasing member being configured to bias the switch button toward a side of the button top.

10. The push switch device of the endoscope according to claim 1, wherein the flange is configured such that the arc is larger than a size of an outer shape of the pusher.

11. The push switch device of the endoscope according to claim 1, wherein the flange has a circular shape around the shaft.

12. The push switch device of the endoscope according to claim 1, further comprising, a biasing member provided between the flange and a housing body, the biasing member being configured to bias the switch button toward a side of the button top.

13. The push switch device of the endoscope according to claim 1, wherein the case body forms an outer surface of the operation portion, and the case body includes an inner surface having a contact surface with which a part of an outer circumferential surface of the flange is brought into contact, when the shaft is tilted.

14. The push switch device of the endoscope according to claim 13, wherein the contact surface is provided in all radial directions around the shaft.

15. The push switch device of the endoscope according to claim 13, wherein the flange is configured such that a part of the arc is brought into contact only with the contact surface when the shaft is tilted.

16. An endoscope comprising:

an operation portion configured to be grasped by an operator; and a push switch device provided at the operation portion, wherein the push switch device comprises:

an operation switch configured to make an electric circuit conductive; and a switch button configured to push the operation switch, and the switch button comprises:

a shaft arranged by being inserted through a hole formed in a case body of the operation portion;

a button top connected to one end of the shaft and arranged outside the case body, the button top being configured to receive an operational force in a direction orthogonal to the shaft;

a pusher having a shape including at least a part of a spherical body having an outer diameter larger than an outer diameter of the shaft, the pusher being configured to move when the button top receives the operational force, to push in the operation switch arranged facing the pusher; and a flange provided at midway of the shaft and including an arc which is on an outer surface of the flange and has a diameter larger than an outer diameter of the button top, the flange being housed in an inside of the operation portion and configured such that a part of the outer surface is brought into a state abuttable against the inside of the operation portion when the shaft is tilted by the operational force applied to the button top.

17. The endoscope according to claim 16, wherein the pusher is arranged facing the operation switch such that an outer circumference of the pusher around the shaft is rotatably supported by a housing body provided in the operation portion and configured to hold the switch button.

18. The endoscope according to claim 16, wherein the flange is configured such that the arc is larger than a size of an outer shape of the pusher.

19. The endoscope according to claim 16, wherein the endoscope is a single-use endoscope configured to be used once.

20. The endoscope according to claim 16, wherein a cover that covers an outer surface of the button top to thereby maintain watertightness in the operation portion is fixed to the button top.

\* \* \* \* \*